(12) United States Patent
Takayama et al.

(10) Patent No.: US 12,325,845 B2
(45) Date of Patent: Jun. 10, 2025

(54) INCUBATOR AND METHOD OF OPERATING MICROFLUIDIC DEVICE

(71) Applicant: FUJIFILM CORPORATION, Tokyo (JP)

(72) Inventors: Hidetoshi Takayama, Kanagawa (JP); Koju Ito, Kanagawa (JP); Takahiro Oba, Kanagawa (JP); Keisuke Oku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 929 days.

(21) Appl. No.: 17/462,025

(22) Filed: Aug. 31, 2021

(65) Prior Publication Data

US 2021/0395656 A1    Dec. 23, 2021

Related U.S. Application Data

(63) Continuation of application No. PCT/JP2020/002931, filed on Jan. 28, 2020.

(30) Foreign Application Priority Data

Mar. 12, 2019   (JP) .................................. 2019-044496

(51) Int. Cl.
*C12M 1/00*   (2006.01)
*C12M 3/00*   (2006.01)
*C12M 3/06*   (2006.01)

(52) U.S. Cl.
CPC ............ *C12M 1/005* (2013.01); *C12M 41/14* (2013.01); *C12M 23/16* (2013.01); *C12M 23/44* (2013.01); *C12M 23/48* (2013.01); *C12M 23/50* (2013.01)

(58) Field of Classification Search
CPC ............................. C12M 1/005; C12M 41/14
See application file for complete search history.

(56) References Cited

U.S. PATENT DOCUMENTS

| | | | |
|---|---|---|---|
| 2005/0113668 A1* | 5/2005 | Srinivasan | ............. A61B 5/416 |
| | | | 600/422 |
| 2008/0240995 A1 | 10/2008 | Murakami | |
| 2018/0105787 A1 | 4/2018 | Hardin | |

FOREIGN PATENT DOCUMENTS

| | | | | |
|---|---|---|---|---|
| JP | 2002319577 A | * | 10/2002 | |
| JP | 2004007851 A | * | 1/2004 | ............. H02J 50/12 |

(Continued)

OTHER PUBLICATIONS

Extended European Search Report dated May 11, 2022, issued in corresponding EP Patent Application No. 20769847.3.

(Continued)

*Primary Examiner* — Elizabeth A Robinson
*Assistant Examiner* — Jonathan E Lepage
(74) *Attorney, Agent, or Firm* — SOLARIS Intellectual Property Group, PLLC (57) ABSTRACT

There is provided an incubator including an accommodation space that is shielded from an external environment, an environmental control unit that controls an environment of the inside of the accommodation space, a power supply unit that is provided in the accommodation space and transmits electric power to a power supply target in a noncontact state, and a partition wall that is provided in the accommodation space and shields electromagnetic waves radiated from the power supply unit.

9 Claims, 6 Drawing Sheets

(56) References Cited

FOREIGN PATENT DOCUMENTS

| JP | 2006-145153 A | 6/2006 |
|----|---------------|--------|
| JP | 2011-163993 A | 8/2011 |
| JP | 2012-016250 A | 1/2012 |
| JP | 2013-132134 A | 7/2013 |
| JP | 2013-228220 A | 11/2013 |
| WO | 2007/066478 A1 | 6/2007 |
| WO | 2011/099386 A1 | 8/2011 |
| WO | 2016/043216 A1 | 3/2016 |

OTHER PUBLICATIONS

English language translation of the following: Office action dated Aug. 30, 2022 from the JPO in a Japanese patent application No. 2021-505573 corresponding to the instant patent application. This office action translation is submitted now in order to supplement the understanding of the cited reference which is being disclosed in the instant Information Disclosure Statement.
Office Action dated Dec. 20, 2023, issued by the EPO in corresponding EP Patent Application No. 20769847.3.
International Search Report issued in International Application No. PCT/JP2020/002931 on Apr. 14, 2020.
Written Opinion of the ISA issued in International Application No. PCT/JP2020/002931 on Apr. 14, 2020.
English language translation of the following: Decision of Refusal dated Jan. 17, 2023 from the JPO in a Japanese patent application No. 2021-505573 corresponding to the instant patent application.

\* cited by examiner

INCUBATOR AND METHOD OF OPERATING MICROFLUIDIC DEVICE

CROSS-REFERENCE TO RELATED APPLICATIONS

This application is a continuation application of International Application No. PCT/JP2020/002931, filed Jan. 28, 2020, the disclosure of which is incorporated herein by reference in its entirety. Further, this application claims priority from Japanese Patent Application No. 2019-044496, filed on Mar. 12, 2019, the disclosure of which is incorporated herein by reference in its entirety.

BACKGROUND

1. Technical Field

The disclosed technology relates to an incubator and a method of operating a microfluidic device.

2. Description of the Related Art

The following technologies are known as the technology related to a device that controls an environment in an accommodation space to a predetermined state. For example, JP2006-145153A discloses an article storage device which includes a power source device on a supply side, which is provided in a storage space of a main body of the article storage device and outputs supplied electric power and a power source device on a reception side, which is provided in at least one storage container and receives electric power that is supplied from the power source device on the supply side, in a state of being installed in the storage space, where each of the power source devices on a supply side and the power source device on a reception side is a noncontact type power source device.

SUMMARY

By the way, a microfluidic device is a device in which a micro flow channel or a reaction container is manufactured using a microfabrication technology such as micro electro mechanical systems (MEMS) technology and is expected to be applied in a wide range of fields such as drug discovery, toxicity evaluation, organ-on-chip, body-on-chip, and analytical chemistry. In the evaluation and analysis of cells using a microfluidic device, it is considered that electric devices such as various sensors for obtaining information on cells accommodated inside the microfluidic device and a pump for feeding a liquid to the microfluidic device, and a power source for supplying electric power to these electric devices are accommodated inside the incubator, together with the microfluidic device. Further, in a case where a wireless power supply is used as a method of supplying electric power from a power source to an electric device, the number of wires in the incubator can be reduced.

The wireless power supply by a magnetic field coupling method such as an electromagnetic coupling method or a magnetic field resonance method is a method of contactlessly transmitting electric power, in which a power reception coil receives a magnetic field generated by a power transmission coil. However, in the wireless power supply by an electromagnetic coupling method, electric devices such as various sensors and a pump may malfunction due to electromagnetic waves radiated from a power supply unit having a power transmission coil. In addition, the electromagnetic waves radiated from a power supply unit may have some effect on cells in the microfluidic device.

The disclosed technology was made in consideration of the above points and aims to suppress the influence of the electromagnetic waves radiated from a power supply unit, in an incubator having a power supply unit that transmits electric power to a power supply target in a noncontact state in an accommodation space therein.

An incubator according to the disclosed technology includes an accommodation space that is shielded from an external environment, an environmental control unit that controls an environment of the inside of the accommodation space, a power supply unit that is provided in the accommodation space and transmits electric power to a power supply target in a noncontact state, and a partition wall that is provided in the accommodation space and shields electromagnetic waves radiated from the power supply unit.

According to the incubator according to the disclosed technology, it is possible to suppress the influence of the electromagnetic waves radiated from the power supply unit.

The incubator according to the disclosed technology may further include a stage that is provided in the accommodation space, and a power reception unit that is provided so that a gap is present between the stage and the power reception unit and receives electric power that is supplied from the power supply unit in the noncontact state. In this case, the power supply unit may be attached at a position of the stage facing the power reception unit, and the partition wall may surround a space formed between the power supply unit and the power reception unit.

Further, the incubator according to the disclosed technology may further include a placing stand that is provided so that a gap is present between the stage and the placing stand, and a spacer that is attached to the placing stand and forms a space between the stage and the placing stand. In this case, the power reception coil may be attached to the placing stand.

In a case where an incubator includes a power reception unit, it is possible to supply electric power to an electric device accommodated inside the accommodation space of the incubator through the power reception unit. Further, in a case where a partition wall surrounds the space formed between the power supply unit and the power reception unit, it is possible to suppress the influence of the electromagnetic waves radiated from the power supply unit on the electric device without blocking the electric power transmission carried out between the power supply unit and the power reception unit.

The incubator according to the disclosed technology may further include a positioning member that is provided on the stage and determines the arrangement of the placing stand on the stage. The positioning between the power supply unit and the power reception unit is completed by carrying out the positioning of the placing stand using the positioning member, and thus the occurrence of the misregistration between the power supply unit and the power reception unit can be prevented. This makes it possible to suppress a decrease in the electric power transmission efficiency due to the misregistration between the power supply unit and the power reception unit.

The incubator according to the disclosed technology may include a plurality of power supply units. This makes it possible to accommodate a multi-channel system in the accommodation space of the incubator.

The method of operating the microfluidic device according to the disclosed technology includes accommodating an electric device and a microfluidic device connected to the electric device in the accommodation space of the incubator to operate the microfluidic device, where the electric device is operated by receiving electric power that is supplied from the power supply unit.

The method of operating the microfluidic device according to the disclosed technology includes placing an electric device and a microfluidic device electric device on the placing stand of the incubator to operate the microfluidic device, where the electric device is operated by receiving electric power that is supplied from the power reception unit and.

The method of operating a microfluidic device according to the disclosed technology may include accommodating cells in the microfluidic device.

According to the method of operating a microfluidic device according to the disclosed technology, since the electromagnetic waves radiated from the power supply unit are shielded by the partition wall, it is possible to suppress a risk that the electric device malfunctions due to the influence of the electromagnetic waves. In addition, it is possible to suppress the influence of the electromagnetic waves radiated from the power supply unit on cells in the microfluidic device.

According to the disclosed technology, it is possible to suppress the influence of the electromagnetic waves radiated from a power supply unit, in an incubator having a power supply unit that transmits electric power to a power supply target in a noncontact state in an accommodation space therein.

BRIEF DESCRIPTION OF THE DRAWINGS

Exemplary embodiments according to the technique of the present disclosure will be described in detail based on the following figures, wherein.

DETAILED DESCRIPTION

Hereinafter, one example of the embodiment of the present invention will be described with reference to the drawings. In each drawing, the same or equivalent configuration elements or parts are designated by the same reference numeral, and duplicate descriptions will be omitted as appropriate.

First Embodiment

Figure 1:
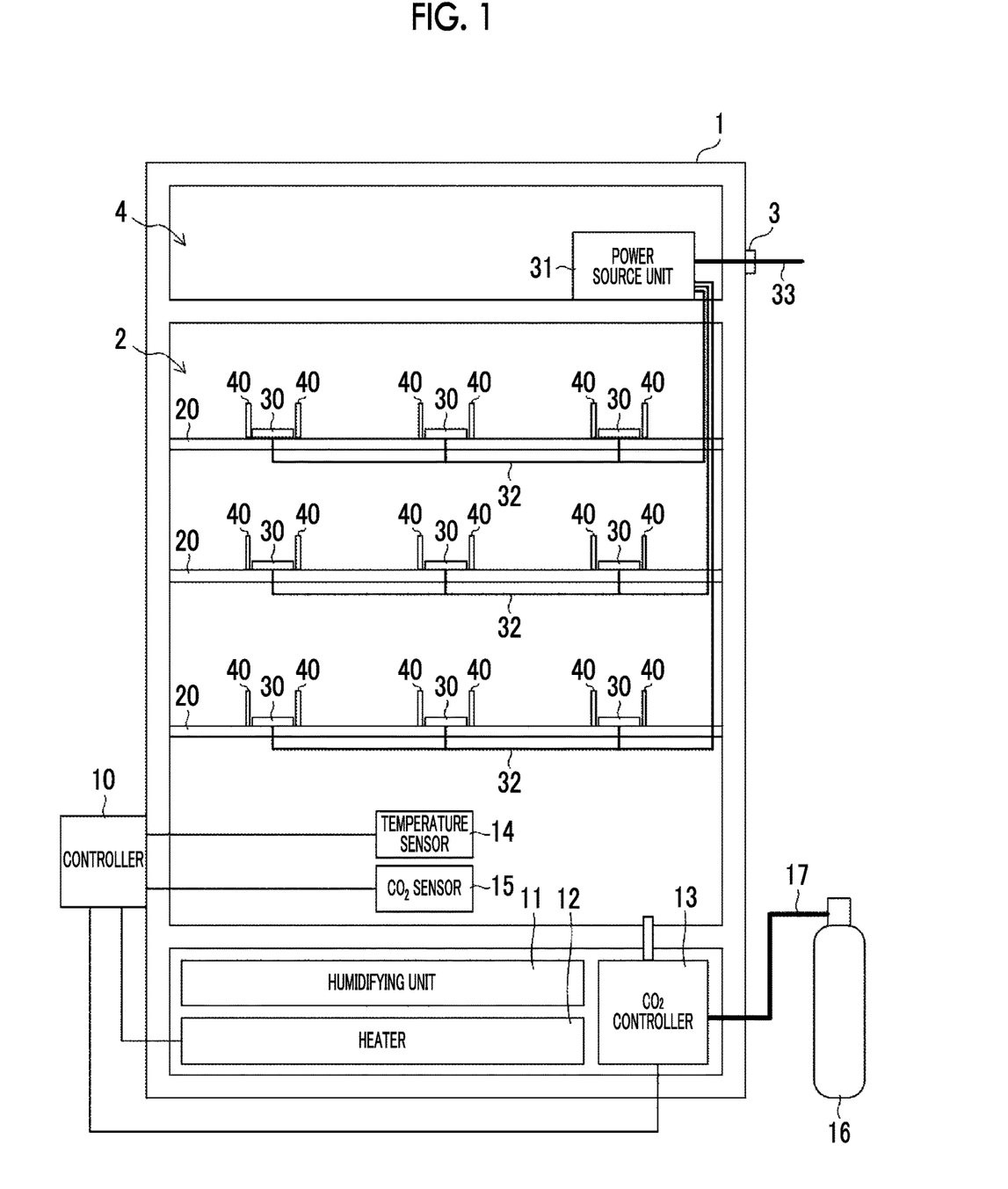
FIG. 1 is a view illustrating an example of an internal configuration of an incubator according to an embodiment of the disclosed technology.

FIG. 1 is a view illustrating an example of an internal configuration of an incubator 1 according to a first embodiment of the disclosed technology.

The incubator 1 has the accommodation space 2 shielded from the external environment. The incubator 1 has a controller 10, a humidifying unit 11, a heater 12, a $CO_2$ controller 13, a temperature sensor 14, and a $CO_2$ sensor 15 as environmental control units for controlling the environment of the accommodation space 2.

The temperature sensor 14 is provided inside the accommodation space 2, detects the temperature in the accommodation space 2, and supplies a detection signal indicating the detected temperature to the controller 10. The $CO_2$ sensor 15 is provided inside the accommodation space 2, detects the $CO_2$ concentration in the accommodation space 2, and supplies a detection signal indicating the detected $CO_2$ concentration to the controller 10.

The controller 10 controls the heater 12 so that the temperature in the accommodation space 2 becomes the temperature specified by a user, based on the temperature detected by the temperature sensor 14. Further, the controller 10 controls the $CO_2$ controller 13 so that the $CO_2$ concentration in the accommodation space 2 becomes the concentration specified by a user, based on the $CO_2$ concentration detected by the $CO_2$ sensor 15. The $CO_2$ controller 13 is connected to a $CO_2$ cylinder 16, which is installed outside the incubator 1, through a pipe 17, and adjusts the amount of $CO_2$ gas that is released into the inside of the accommodation space 2 based on the control by the controller 10, where the $CO_2$ gas is supplied from the $CO_2$ cylinder 16.

The humidifying unit 11 has a configuration in which a vat in which water is stored is included, and the humidity in the accommodation space 2 is maintained above a predetermined value due to the spontaneous vaporization of the water in the vat.

A stage 20 arranged in multiple stages is provided in the accommodation space 2. A plurality of power supply units 30 are mounted on the upper surface of each of the stages 20. In the example illustrated in FIG. 1, a case where three power supply units 30 are mounted on each of the three stages 20 is illustrated; however, the number of stages of the stage 20 and the number of power supply units 30 mounted on each of the stages 20 can be increased or decreased as appropriate. The power supply unit 30 is a wireless power supply unit that transmits electric power, in a noncontact state, to a power supply target (that is, a power reception unit) which is not illustrated in the drawing. As the electric power transmission method in the power supply unit 30, a magnetic field coupling method such as an electromagnetic coupling method or a magnetic field resonance method is applied. Accordingly, the power supply unit 30 has a configuration in which a power transmission coil (not illustrated in the drawing) is included. The wireless power supply by a magnetic field coupling method is a method of contactlessly transmitting electric power in which a power reception coil receives a magnetic field generated by a power transmission coil. As the power supply unit 30, for example, a power supply unit having an output of about 100 kHz to several hundred kHz and 5 W to 15 W according to the Qi standard is used.

Each of the power supply units 30 is connected to the power source unit 31 through the power supply line 32, and electric power is supplied from the power source unit 31, whereby a current flows to the power transmission coil (not illustrated in the drawing) to generate a magnetic field. The power source unit 31 is arranged in a shielded space 4 that is shielded from the accommodation space 2. The humidity in the shielded space 4 is set to be the same level as that of the humidity outside the incubator 1 and is lower than the humidity in the accommodation space 2 that is maintained at a relatively high humidity. Since the power source unit 31 is arranged in the shielded space 4, the power source unit 31 is prevented from being exposed to a high humidity environment, and the occurrence of problems such as electric leakage is suppressed. The power supply line 33 for supplying electric power to the power source unit 31 is led out to the outside of the incubator 1 through the access port 3 that is provided on the wall surface of the incubator 1. Here, in a case where the number of power supply lines that are led out to the outside of the incubator 1 is increased, the risk of foreign matters such as dust and bacteria being mixed into the inside of the accommodation space 2 of the incubator 1 increases. In a case where electric power is distributed from the power source unit 31 accommodated inside the incubator 1 to a plurality of power supply units 30 through the power supply line 32, the number of power supply lines that are led out to the outside of the incubator 1 can be reduced to one, and thus the risk of the inside of the accommodation space 2 being contaminated can be suppressed.

Figure 2:
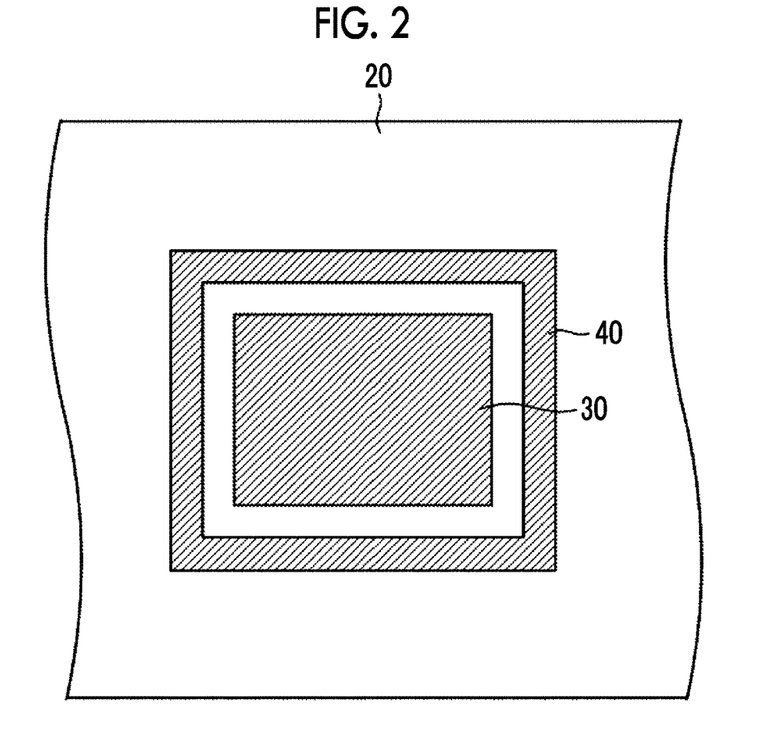
FIG. 2 is a top view of a power supply unit and a partition wall that are mounted on a stage according to the embodiment of the disclosed technology.

A partition wall 40 that shields electromagnetic waves radiated from the power supply unit 30 is provided on the stage 20. The partition wall 40 is provided to correspond to each of the power supply units 30. FIG. 2 is a top view of the power supply unit 30 and the partition wall 40 that are mounted on the stage 20. The partition wall 40 has a ring shape that surrounds the corresponding power supply unit 30. The partition wall 40 is made of a material capable of shielding electromagnetic waves radiated from the power supply unit 30 during the operation of the power supply unit 30, for example, an electric conductor. Specifically, a metal such as aluminum, copper, iron, or stainless steel can be used as the material of the partition wall 40. Further, as the material of the partition wall 40, it is also possible to use a material obtained by forming a conductive film on the surface of the resin. It is possible to use conductive ink as the material of the conductive film. It is preferable that each of the partition walls 40 is connected to a fixed potential such as a ground potential. Each of the partition walls 40 may be electrically connected to, for example, the housing of the incubator 1.

Figure 3A:
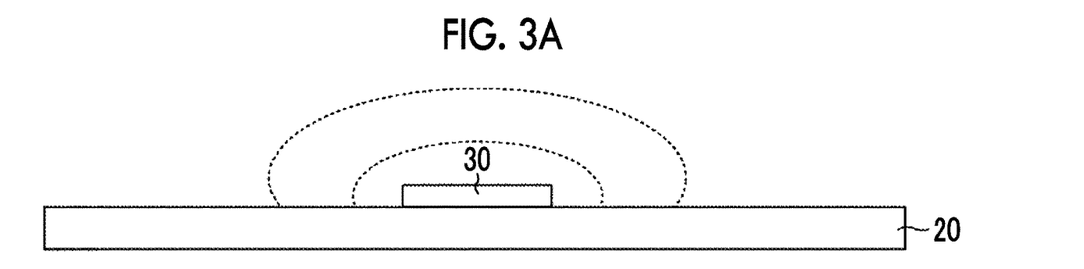
FIG. 3A is a view schematically illustrating electromagnetic waves radiated from the power supply unit according to the embodiment of the disclosed technology.
Figure 3B:
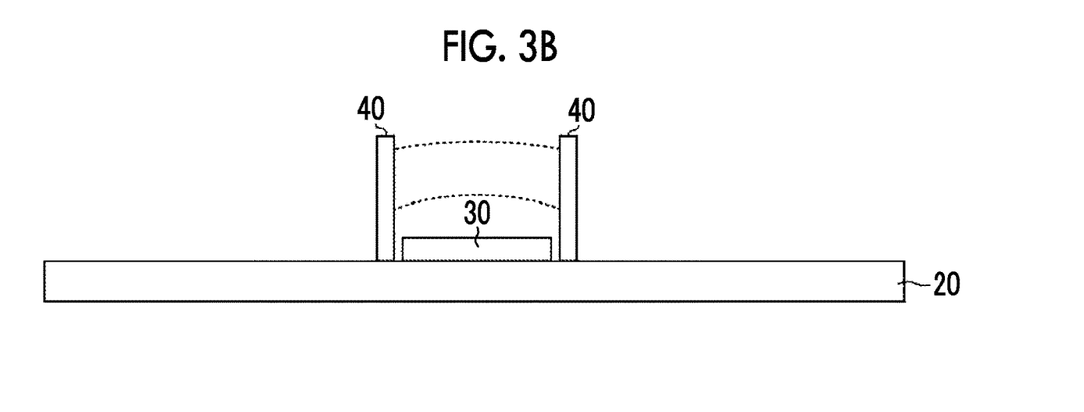
FIG. 3B is a view schematically illustrating electromagnetic waves radiated from the power supply unit according to the embodiment of the disclosed technology.

FIG. 3A is a view schematically illustrating electromagnetic waves radiated from the power supply unit 30 mounted on the stage 20. During the operation of the power supply unit 30, the electromagnetic waves radiated from the power supply unit 30 spread radially as illustrated in FIG. 3A. In a case where the partition wall 40 that shields electromagnetic waves radiated from the power supply unit 30 is not present, the electromagnetic waves radiated from the power supply unit 30 affect the electric device (not illustrated in the drawing) arranged in the vicinity of the power supply unit 30, whereby the electric device may malfunction. As illustrated in FIG. 3B, in a case where the partition walls 40 that shields the electromagnetic waves radiated from the power supply unit 30 is provided to correspond to each of the power supply units 30, the range affected by the electromagnetic waves radiated from the power supply unit 30 can be reduced, and thus it is possible to suppress the influence on the electric device arranged in the vicinity of the power supply unit 30.

As described above, according to the incubator 1 according to the embodiment of the disclosed technology, since the power supply unit 30 is provided in the accommodation space 2, it is possible, for example, to accommodate, in the incubator 1 together with the microfluidic device, electric devices such as various sensors for obtaining information on cells accommodated inside the microfluidic device and a pump for feeding a liquid to the microfluidic device and to supply electric power to the electric devices by using the power supply unit 30. In a case where a wireless power supply is used as a method of supplying electric power to the above electric devices, the number of wires in the accommodation space 2 in the incubator 1 can be reduced.

Further, according to the incubator 1 according to the embodiment of the disclosed technology, since the partition wall 40 that shields the electromagnetic waves radiated from the power supply unit 30 is provided to correspond to each of the power supply units 30, it is possible to suppress a risk that the above electric devices malfunction due to the electromagnetic waves radiated from the power supply unit 30. In addition, it is possible to suppress the influence of the electromagnetic waves radiated from the power supply unit 30 on cells that are accommodated in the microfluidic device.

Second Embodiment

Figure 4:
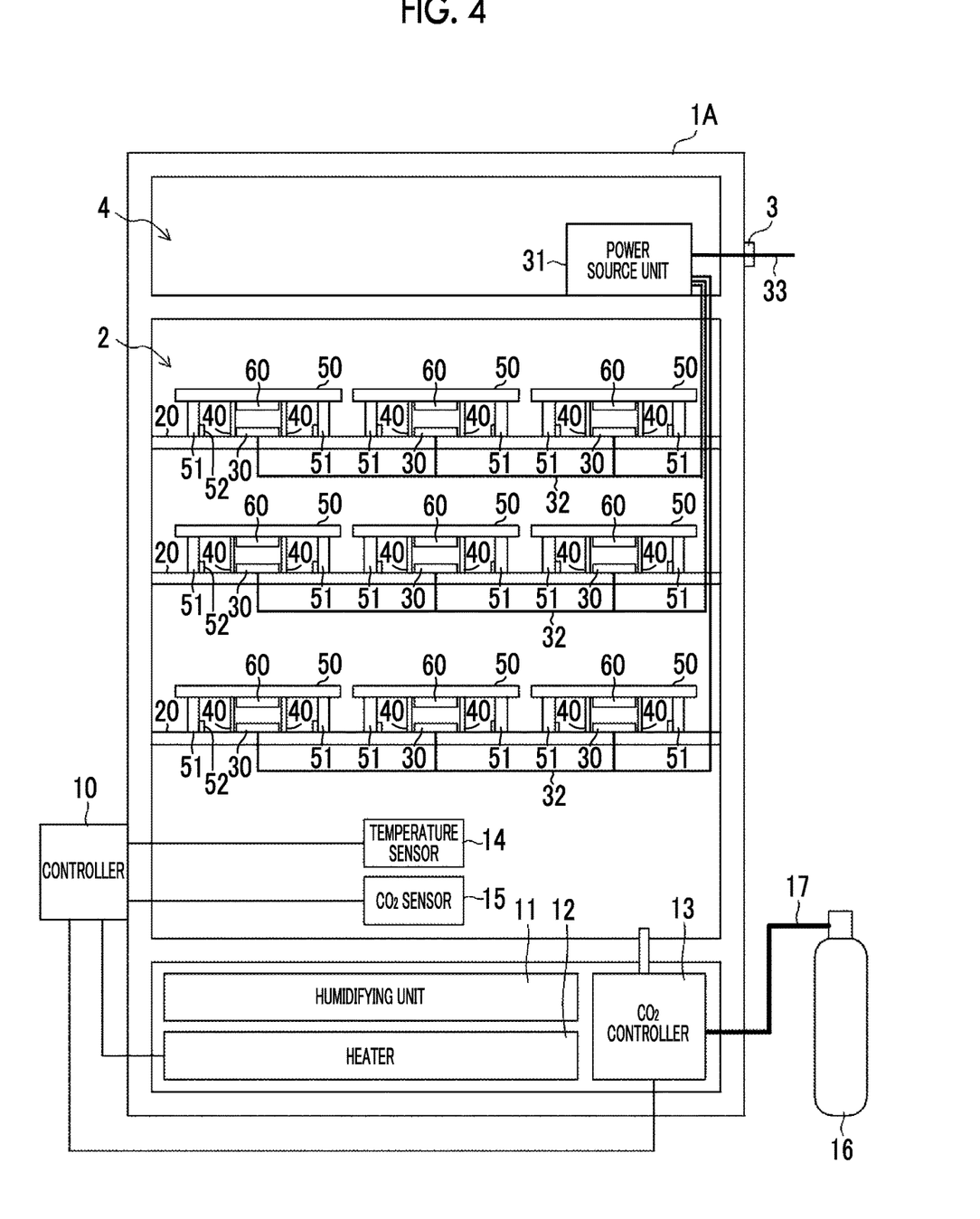
FIG. 4 is a view illustrating an example of an internal configuration of an incubator according to another embodiment of the disclosed technology.

FIG. 4 is a view illustrating an example of an internal configuration of an incubator 1A according to a second embodiment of the disclosed technology.

The stage 20 arranged in multiple stages is provided in the accommodation space 2 of the incubator 1A. A plurality of power supply units 30 are mounted on the upper surface of each of the stages 20. Further, on the stage 20, a plurality of placing stands 50 are provided to correspond to each of the power supply units 30. A spacer 51 for forming a space between the stage 20 and the placing stand 50 is attached to each of the placing stands 50. That is, the placing stand 50 is provided so that a gap is present between the placing stand 50 and the stage 20.

On the lower surface of each of the placing stands 50 (the surface facing the stage 20), a power reception unit 60 that receives electric power that is supplied from the corresponding power supply unit 30 in a noncontact state is provided. That is, each of the power reception units 60 is provided so that a gap is present between the stage 20 and the corresponding power supply unit 30. Each of the power reception units 60 is arranged at a position (that is, a position overlapping when seen in a plan view) facing the corresponding power supply unit 30. In other words, each of the power supply units 30 is attached at a position of the stage 20 facing the power reception unit 60. Each of the power reception units 60 has a configuration in which a power reception coil (not illustrated in the drawing) that receives a magnetic field generated by a power transmission coil which constitutes the power supply unit 30 is included.

A positioning member 52 for determining the arrangement of the placing stand 50 on the stage is provided on the stage 20. The positioning member 52 may be composed of, for example, a protruding structure that protrudes from the upper surface of the stage 20, and the placing stand 50 may be positioned by bringing the spacer 51 that has been attached to the placing stand 50 into contact with the protruding structure. In a case where the arrangement of the placing stand 50 is determined according to the positioning member 52, the arrangement of the placing stand 50 and the power reception unit 60 is determined, whereby the power reception unit 60 is arranged at a position facing the power supply unit 30. For the spacer 51, a spacer having an appropriate height is appropriately used so that the distance between the power supply unit 30 and the power reception unit 60 becomes a distance (for example, several mm to 100 mm) in which electric power transmission can be suitably carried out between the power supply unit 30 and the power reception unit 60.

The space formed between each of the power supply units 30 and the corresponding power reception unit 60 is surrounded by the partition wall 40 that shields electromagnetic waves radiated from the power supply unit 30. That is, the pair of the power supply unit 30 and the power reception unit 60 is arranged inside the space surrounded by the partition wall 40. The partition wall 40 may be attached to the lower surface of the placing stand 50 or may be attached to the upper surface of the stage 20. The placing stand 50, the spacer 51, the power reception unit 60, and the partition wall 40 may constitute an integrated unit.

On the upper surface of each of the placing stands 50 (the surface opposite to the surface facing the stage 20), it is possible to mount various electric devices that are operated by receiving electric power that is supplied from the power reception unit 60 and various devices that are used together with these electric devices. For example, on the upper surface of the placing stand 50, it is possible to mount electric devices such as various sensors for obtaining information on cells accommodated inside the microfluidic device and a pump for feeding a liquid to the microfluidic device, together with the microfluidic device.

Figure 5A:
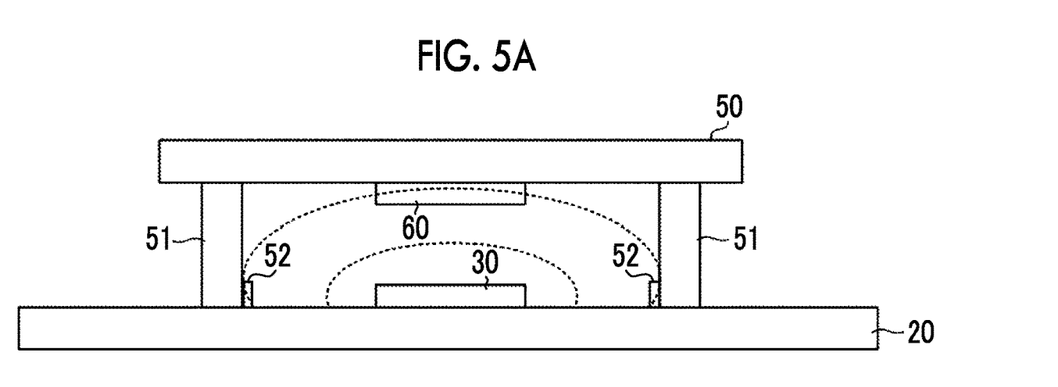
FIG. 5A is a view schematically illustrating electromagnetic waves radiated from the power supply unit according to the embodiment of the disclosed technology.

FIG. 5A is a view schematically illustrating electromagnetic waves radiated from the power supply unit 30 mounted on the stage 20. During the operation of the power supply unit 30, the electromagnetic waves radiated from the power supply unit 30 spread radially as illustrated in FIG. 5A. In a case where the partition wall 40 that shields electromagnetic waves radiated from the power supply unit 30 is not present, the electromagnetic waves radiated from the power supply unit 30 affect the electric device (not illustrated in the drawing) mounted on the placing stand 50, whereby the electric device may malfunction.

Figure 5B:
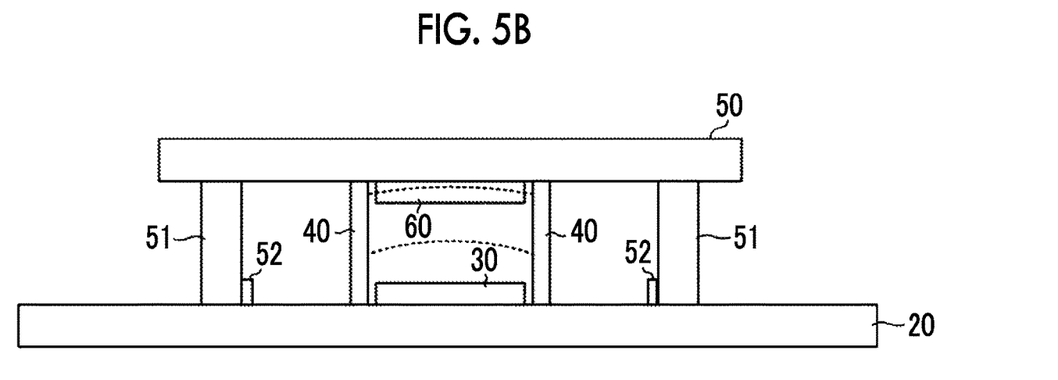
FIG. 5B is a view schematically illustrating electromagnetic waves radiated from the power supply unit according to the embodiment of the disclosed technology.

However, as illustrated in FIG. 5B, in a case where the space formed between the power supply unit 30 and the power reception unit 60 is surrounded by the partition wall 40, the range affected by the electromagnetic waves radiated from the power supply unit 30 can be reduced, and thus it is possible to suppress the influence on the electrical device mounted on the placing stand 50.

On the other hand, since the pair of the power supply unit 30 and the power reception unit 60 is arranged in the inside of the space surrounded by the partition wall 40, the electric power transmission carried out between the power supply unit 30 and the power reception unit 60 is not blocked by the partition wall 40.

As described above, according to the incubator 1A according to the second embodiment of the disclosed technology, the same effect as that of the incubator 1 according to the first embodiment can be obtained. Further, since the power reception unit 60 that receives electric power that is supplied from the power supply unit 30 in a noncontact state is provided in the accommodation space 2, it is possible to supply electric power to the electric device accommodated inside the accommodation space 2 by using the power reception unit 60.

Further, according to the incubator 1A according to the second embodiment of the disclosed technology, the power reception unit 60 is provided on the lower surface of the placing stand 50 having the spacer 51, and thus it is possible to carry out the positioning of the placing stand 50 with the positioning member 52 that is provided on the stage 20. That is, the positioning between the power supply unit 30 and the power reception unit 60 is completed by carrying out the positioning of the placing stand 50 using the positioning member 52, and thus the occurrence of the misregistration between the power supply unit 30 and the power reception unit 60 can be prevented. This makes it possible to suppress a decrease in the electric power transmission efficiency due to the misregistration between the power supply unit 30 and the power reception unit 60.

Figure 6:
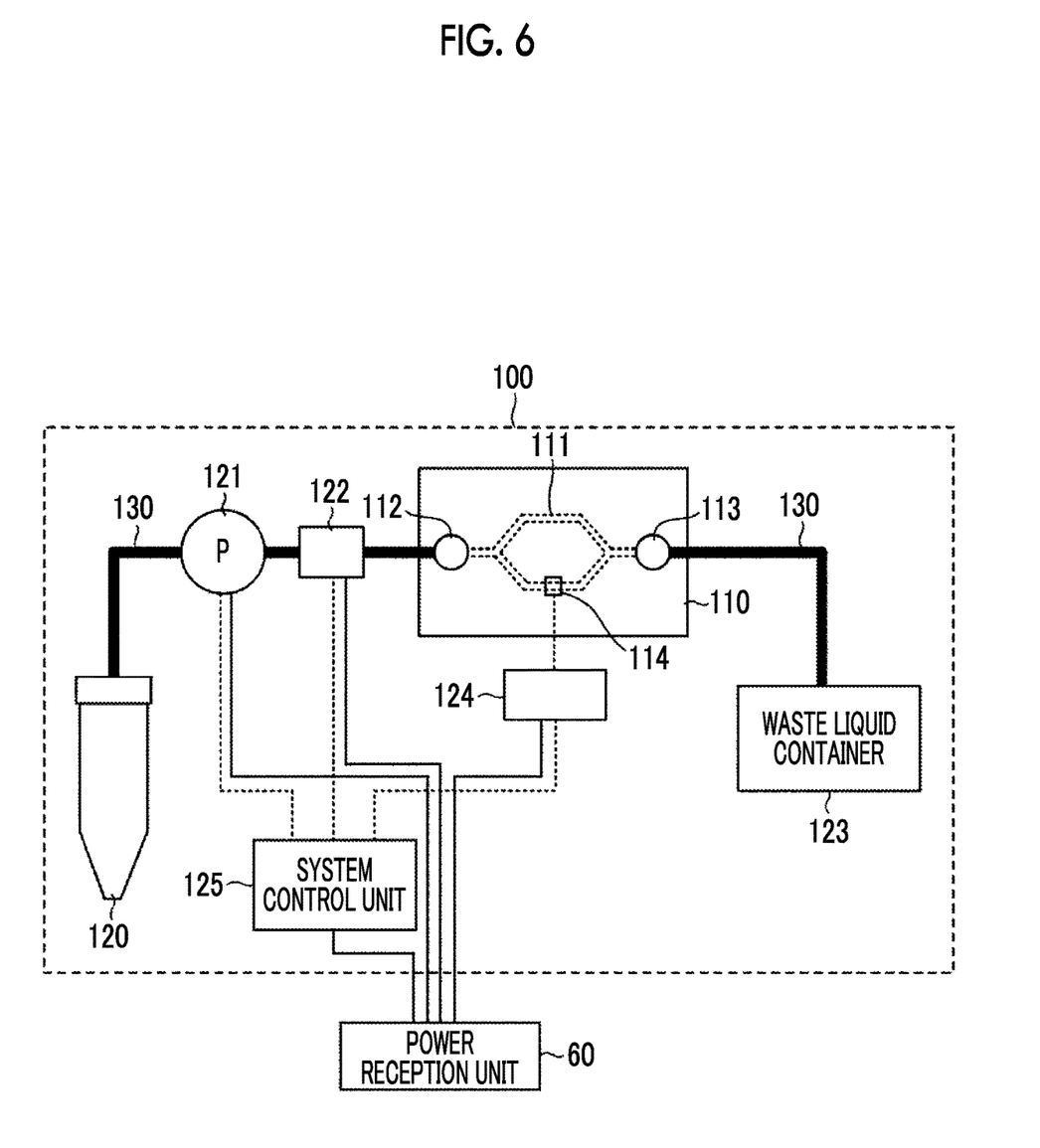
FIG. 6 is a view illustrating an example of a configuration of a cell culture system, in which a microfluidic device according to the embodiment of the disclosed technology is included.

FIG. 6 is a view illustrating an example of a configuration of a cell culture system 100, in which a microfluidic device 110 is included. The cell culture system 100 has a configuration in which the microfluidic device 110, a storage container 120, a pump 121, a flow rate sensor 122, an impedance measuring instrument 124, a waste liquid container 123, a system control unit 125, and a pipe 130 are included.

The microfluidic device 110 has a micro flow channel 111 that is formed by using a microfabrication technology such as MEMS technology, an inflow port 112 that is provided at one end of the micro flow channel 111, and an outflow port 113 that is provided at the other end of the micro flow channel 111. Further, the microfluidic device 110 has an electrode 114 that is provided in the middle of the micro flow channel 111. In cell culture using the cell culture system 100, cells are arranged inside the micro flow channel 111, and then the cells are cultured.

The storage container 120 is connected to the inflow port 112 through the pipe 130. The pump 121 and the flow rate sensor 122 are provided in the middle of the pipe 130. The storage container 120 stores a liquid such as a medium, additives, and reagents, which is used for culturing cells accommodated in the microfluidic device 110. The cell culture system 100 may have a plurality of storage containers respectively storing a plurality of different kinds of liquids are included or may have a configuration such that liquids accommodated inside a plurality of storage containers can be selectively supplied to the microfluidic device 110.

The pump 121 carries out feeding of a liquid such as a medium stored in the storage container 120. In a case where the pump 121 is driven, the liquid accommodated in the storage container 120 is supplied to the micro flow channel 111 through the inflow port 112. The flow rate sensor 122 detects the flow rate of the liquid supplied to the microfluidic device 110 per unit time and outputs a detection signal indicating the detected flow rate. The liquid supplied to the micro flow channel 111 flows out from the outflow port 113 and is collected in the waste liquid container 123 through the pipe 130.

The impedance measuring instrument 124 is connected to the electrode 114 that is provided in the middle of the micro flow channel 111 and outputs an impedance value depending on the state of cells that are cultured on the micro flow channel 111 based on an electric signal supplied from the electrode 114. The above impedance value may correspond to, for example, a transepithelial electrical resistance value.

The system control unit 125 controls the drive of the pump 121 based on the detection signal output from the flow rate sensor 122. That is, the system control unit 125 controls the feeding amount of liquid in the pump 121 so that the flow rate of the liquid per unit time, which is indicated by the detection signal output from the flow rate sensor 122, becomes a predetermined value. Further, the system control unit 125 carries out control for recording the impedance value measured by the impedance measuring instrument 124 and transmitting it to the external system.

The electric device including the pump 121, the flow rate sensor 122, the impedance measuring instrument 124, and the system control unit 125 is operated by receiving electric power that is supplied from the power reception unit 60.

Figure 7:
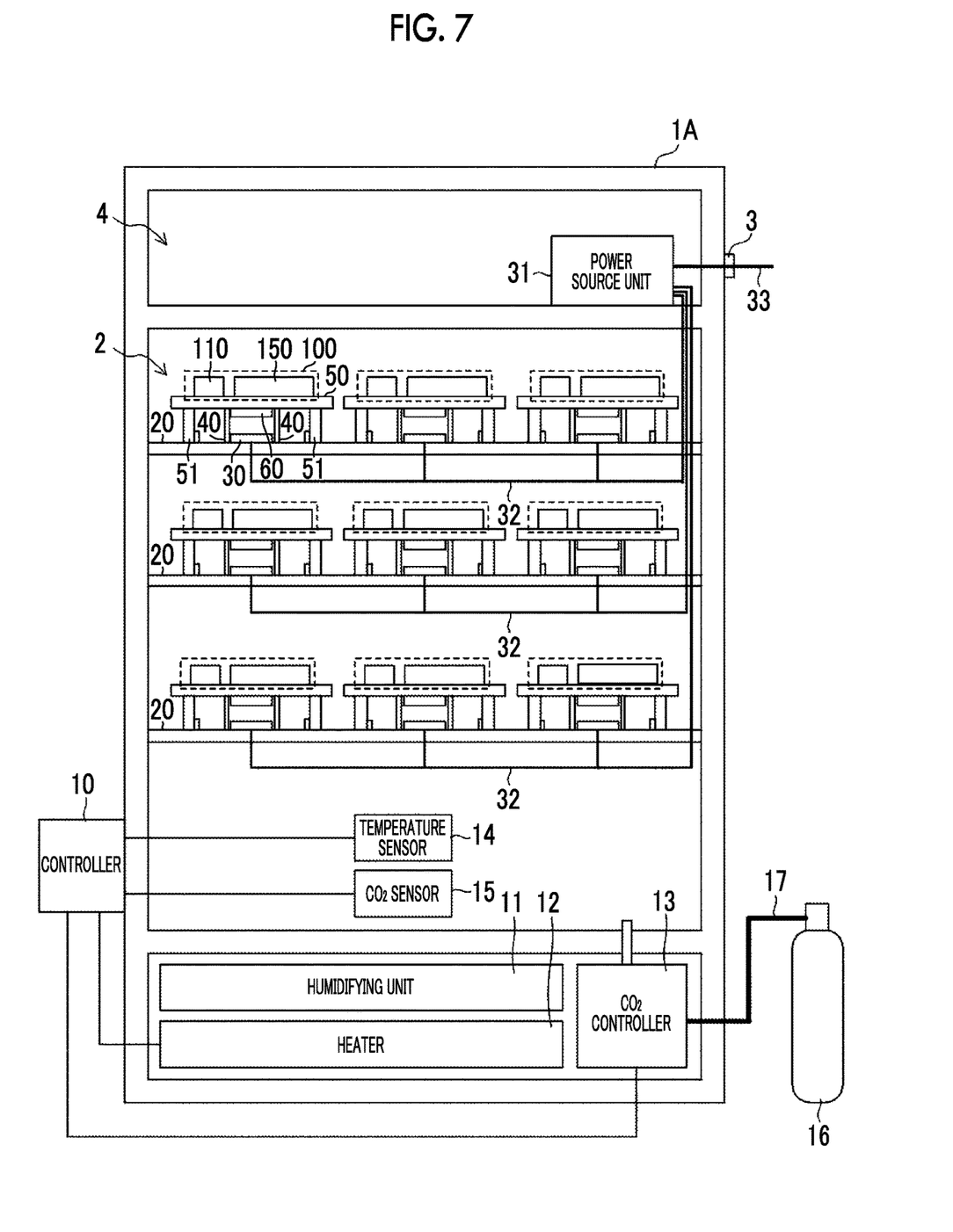
FIG. 7 is a view illustrating an example of a method of operating a microfluidic device, where the method uses the incubator according to the embodiment of the disclosed technology.

FIG. 7 is a view illustrating an example of a method of operating the microfluidic device 110, where the method uses the incubator 1A.

On each of the plurality of placing stands 50 that are provided in the accommodation space 2 of the incubator 1A, the electric device 150 including the pump 121, the flow rate sensor 122, the impedance measuring instrument 124, and the system control unit 125, and the cell culture system 100 having the microfluidic device 110 are mounted. That is, in the accommodation space 2 of the incubator 1A, a multi-channel cell culture system 100 is arranged to correspond to each pair of the power supply unit 30 and the power reception unit 60. The electric device 150 in each channel is operated by receiving electric power that is supplied from a power reception unit 60 provided on the placing stand 50 on which the electric device 150 is mounted.

As described above, the method of operating the microfluidic device 110 according to the embodiment of the disclosed technology includes accommodating the electric device 150 and the microfluidic device 110 in the accommodation space 2 of the incubator 1A to operate the microfluidic device 110, where the electric device 150 is operated by receiving electric power that is supplied from the power supply unit 30 and the microfluidic device 110 is connected to the electric device 150. More specifically, the above method includes placing the electric device 150 and the microfluidic device 110 on the placing stand 50 to operate the microfluidic device 110, where the electric device 150 is operated by receiving electric power that is supplied from the power reception unit 60 provided on the placing stand 50 and the microfluidic device 110 is connected to the electric device 150.

According to the method of operating the microfluidic device 110 according to the embodiment of the disclosed technology, since the electromagnetic waves radiated from the power supply unit 30 are shielded by the partition wall 40, it is possible to suppress a risk that the electric device 150 malfunctions due to the influence of the electromagnetic waves. In addition, it is possible to suppress the influence of the electromagnetic waves radiated from the power supply unit 30 on cells in the microfluidic device 110.

The disclosure of JP2019-044496 filed on Mar. 12, 2019, is incorporated in the present specification in its entirety by reference. In addition, all documents, patent applications, and technical standards described in the present specification are incorporated in the present specification by reference, to the same extent as in the case where each of the documents, patent applications, and technical standards is specifically and individually described.

What is claimed is:

1. An incubator comprising:
an accommodation space that is shielded from an external environment;
an environmental control unit that controls an environment of an inside of the accommodation space;
a power reception unit
a power supply unit that is provided in the accommodation space and transmits electric power to the power reception unit in a noncontact state;
a partition wall that is provided in the accommodation space and shields electromagnetic waves radiated from the power supply unit; and
a stage that is provided in the accommodation space; wherein
the power reception unit that is provided does not contact the stage so that a gap is present between the stage and the power reception unit and receives electric power that is supplied from the power supply unit in the noncontact state,
the power supply unit is attached at a position of the stage facing the power reception unit, and
the partition wall surrounds a space formed between the power supply unit and the power reception unit.

2. The incubator according to claim 1, further comprising:
a placing stand that is provided so that a gap is present between the stage and the placing stand; and
a spacer that is attached to the placing stand and forms a space between the stage and the placing stand,
wherein the power reception unit is attached to the placing stand.

3. The incubator according to claim 2, further comprising:
a positioning member that is provided on the stage and determines arrangement of the placing stand on the stage.

4. The incubator according to claim 1,
wherein a plurality of the power supply units are provided.

5. The incubator according to claim 1, wherein
cells are positioned inside the accommodation space at a position above the space formed between the power supply unit and the power reception unit.

6. The incubator according to claim 1, wherein
an electric device and a microfluidic device connected to the electric device is accommodated in the accommodation space at a position above the space formed between the power supply unit and the power reception unit, the electric device being operated by receiving electric power that is supplied from the power supply unit.

7. A method of operating a microfluidic device, comprising:
accommodating an electric device and a microfluidic device connected to the electric device in the accommodation space of the incubator according to claim 1 to operate the microfluidic device, the electric device being operated by receiving electric power that is supplied from the power supply unit.

8. The method of operating a microfluidic device according to claim 7, further comprising:
accommodating cells in the microfluidic device.

9. A method of operating a microfluidic device, comprising:
placing an electric device and a microfluidic device connected to the electric device on the placing stand of the incubator according to claim 2 to operate the microfluidic device, the electric device being operated by receiving electric power that is supplied from the power reception unit.

* * * * *